(12) United States Patent
Balter et al.

(10) Patent No.: US 11,596,723 B2
(45) Date of Patent: Mar. 7, 2023

(54) INTRADIALYTIC MONITORING OF BLOOD VOLUME CHANGE

(71) Applicant: Fresenius Medical Care Holdings, Inc., Waltham, MA (US)

(72) Inventors: Paul Balter, River Forest, IL (US); Linda Ficociello, Littleton, MA (US); Christina Rossi, Concord, MA (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 451 days.

(21) Appl. No.: 16/730,749

(22) Filed: Dec. 30, 2019

(65) Prior Publication Data

US 2021/0196879 A1 Jul. 1, 2021

(51) Int. Cl.
*A61M 1/30* (2006.01)

(52) U.S. Cl.
CPC ....... *A61M 1/30* (2013.01); *A61M 2205/3379* (2013.01); *A61M 2230/207* (2013.01)

(58) Field of Classification Search
CPC .... A61B 5/14535; A61B 5/6866; A61M 1/30; A61M 1/361; A61M 2205/3313; A61M 2205/3379; A61M 2205/502; A61M 2230/207
See application file for complete search history.

(56) References Cited

U.S. PATENT DOCUMENTS

| | | |
|---|---|---|
| D420,340 S | 2/2000 | Bailer et al. |
| 6,381,635 B1 | 4/2002 | Hoyer et al. |
| D467,252 S | 12/2002 | Lee |
| 7,248,263 B2 | 7/2007 | Freeman et al. |
| 7,974,983 B2 | 7/2011 | Goeldi |
| D694,252 S | 11/2013 | Helm |
| 8,856,668 B2 | 10/2014 | Niesslein et al. |
| D717,328 S | 11/2014 | Lin |
| D732,053 S | 6/2015 | Tomita et al. |
| 9,155,823 B2 | 10/2015 | Tarn et al. |

(Continued)

OTHER PUBLICATIONS

"CLiC Device Profile Guide," Fresenius Medical Care Renal Technologies, https://fmcna.com/content/dam/fmcna/live/support/documents/fluid-management/clic/CLiC_ProfileGuide.pdf (2016).

(Continued)

*Primary Examiner* — Dirk R Bass
(74) *Attorney, Agent, or Firm* — Leydig, Voit & Mayer, Ltd.

(57) ABSTRACT

A system for monitoring percentage change in blood volume (ΔBV %) during dialysis treatment includes a sensor device configured to obtain hematocrit (Hct)-related measurements based on detecting light which has passed through extracorporeal blood of a patient undergoing the dialysis treatment; one or more controllers configured to: determine Hct values based on the Hct-related measurements obtained by the sensor device; determine ΔBV % values based on the determined Hct values; and generate a GUI having a ΔBV % plot based on the determined ΔBV % values; and a display device having a display configured to display the GUI having the ΔBV % plot. Zone indicators are provided on the display to distinguish between a first zone corresponding to a first ΔBV % profile, a second zone corresponding to a second ΔBV % profile, and a third zone corresponding to a third ΔBV % profile.

16 Claims, 7 Drawing Sheets

(56) References Cited

U.S. PATENT DOCUMENTS

| | | |
|---|---|---|
| 9,165,112 B2 | 10/2015 | Doyle et al. |
| D780,199 S | 2/2017 | Croan |
| 9,801,993 B2 | 10/2017 | Barrett et al. |
| D804,496 S | 12/2017 | Wahila et al. |
| D812,634 S | 3/2018 | Tuthill et al. |
| D813,883 S | 3/2018 | Amin et al. |
| D816,689 S | 5/2018 | Chalker et al. |
| D820,288 S | 6/2018 | Howell et al. |
| D872,757 S | 1/2020 | Howell et al. |
| D874,481 S | 2/2020 | Kumar et al. |
| D896,828 S | 9/2020 | Linares et al. |
| D924,910 S | 7/2021 | Laumann et al. |
| 2002/0052820 A1 | 5/2002 | Gatto |
| 2002/0154156 A1 | 10/2002 | Moriwake et al. |
| 2007/0138069 A1 | 6/2007 | Roncadi et al. |
| 2008/0105601 A1 | 5/2008 | Ikeda |
| 2014/0028682 A1 | 1/2014 | Omiya |
| 2017/0180482 A1 | 6/2017 | Wang et al. |
| 2019/0200921 A1 | 7/2019 | Barrett et al. |

OTHER PUBLICATIONS

Fresenius Medical Care Renal Technologies, "2008T Hemodialysis Machine with CLiC™ Device, Training Guide" (2015).
Nikkiso "A Flexible Dialysis System to Drive Advanced Treatments: The Modules of the DBB-07" (2019).
International Patent Application No. PCT/US2020/066498, International Search Report (dated Mar. 18, 2021).
U.S. Appl. No. 29/728,817, filed Mar. 20, 2020.

INTRADIALYTIC MONITORING OF BLOOD VOLUME CHANGE

BACKGROUND

Patients with chronic or acute kidney failure undergo dialysis treatment in order to remove toxins and excess fluids from their blood. Hemodialysis is one of the common forms of dialysis treatment. To perform hemodialysis, blood is taken from a patient through an intake needle or catheter which draws blood from an artery or vein located in a specifically accepted access location—for example, a shunt surgically placed in an arm, thigh, subclavian and the like. The needle or catheter is connected to extracorporeal tubing that is fed to a peristaltic pump and then to a dialyzer that cleans the blood and removes excess fluid. The cleaned blood is then returned to the patient through additional extracorporeal tubing and another needle or catheter. Sometimes, a heparin drip is located in the hemodialysis loop to prevent the blood from coagulating.

As the drawn blood passes through the dialyzer, it travels in straw-like tubes within the dialyzer that serve as semipermeable passageways for the unclean blood. Fresh dialysate solution enters the dialyzer at its downstream end. The dialysate surrounds the straw-like tubes and flows through the dialyzer in the opposite direction of the blood flowing through the tubes. Fresh dialysate collects toxins passing through the straw-like tubes by diffusion and excess fluids in the blood by ultrafiltration. Dialysate containing the removed toxins and excess fluids is disposed of as waste. The red cells remain in the straw-like tubes and their volume count is unaffected by the process.

An optical blood monitoring system may be used during hemodialysis treatment or other treatments involving extracorporeal blood flow. The optical blood monitoring system may use optical techniques to non-invasively measure in real-time the hematocrit and the oxygen saturation level of blood flowing through the hemodialysis system. The blood monitoring system may measure the blood at, for example, a sterile blood chamber attached in-line to the extracorporeal tubing.

Blood chambers along with the tube set and dialyzer are replaced for each patient. The blood chamber is intended for a single use. The blood chamber defines an internal blood flow cavity comprising a substantially flat viewing region and two opposing viewing lenses. Emitters (such as light-emitting diode (LED) emitters) and photodetectors for the optical blood monitoring system are fastened (e.g., by clipping) into place onto the blood chamber over the lenses. Multiple wavelengths of light may be resolved through the blood chamber and the patient's blood flowing through the chamber with a photodetector detecting the resulting intensity of each wavelength.

The preferred wavelengths to measure hematocrit are about 810 nm, which is substantially isobestic for red blood cells, and about 1300 nm, which is substantially isobestic for water. A ratiometric technique may be used to calculate the patient's hematocrit value in real-time based on this light intensity information. The hematocrit value is a percentage determined by the ratio between (1) the volume of the red blood cells in a given whole blood sample and (2) the overall volume of the blood sample.

In a clinical setting, the actual percentage change in blood volume occurring during hemodialysis can be determined, in real-time, from the change in the measured hematocrit. Thus, an optical blood monitoring system is able to non-invasively monitor not only the patient's hematocrit level but also the change in the patient's blood volume in real-time during a hemodialysis treatment session. The ability to monitor real-time change in blood volume helps facilitate safe, effective hemodialysis.

To monitor blood in real-time, emitters and photodetectors may be mounted on two opposing heads of a sensor clip assembly that fits over a blood chamber. For accuracy of the system, the emitters and the photodetectors may be located in a predetermined position and orientation each time the sensor clip assembly is clipped into place over the blood chamber. The predetermined position and orientation ensure that light traveling from the emitters to the photodetectors travels through the lenses of the blood chamber.

The optical blood monitoring system may be calibrated for the specific dimensions of the blood chamber and the specific position and orientation of the sensor clip assembly relative to the blood chamber. For this purpose, the sensor clip assembly may be configured to mate to the blood chamber so that the emitters and the photodetectors are at a predetermined position and orientation relative to one another and to the blood chamber.

An example of an optical blood monitoring system having a sensor clip assembly configured to measure hematocrit and oxygen saturation of extracorporeal blood flowing through a blood chamber is described in U.S. Pat. No. 9,801,993, titled "SENSOR CLIP ASSEMBLY FOR AN OPTICAL MONITORING SYSTEM," which is incorporated by reference in its entirety herein.

SUMMARY

In an exemplary embodiment, the present application provides a system for monitoring percentage change in blood volume ($\Delta BV$ %) during dialysis treatment. The system includes: a sensor device configured to obtain hematocrit (Hct)-related measurements based on detecting light which has passed through extracorporeal blood of a patient undergoing the dialysis treatment; one or more controllers configured to: determine Hct values based on the Hct-related measurements obtained by the sensor device; determine $\Delta BV$ % values based on the determined Hct values; and generate a GUI having a $\Delta BV$ % plot based on the determined $\Delta BV$ % values; and a display device having a display configured to display the GUI having the $\Delta BV$ % plot. Zone indicators are provided on the display to distinguish between a first zone corresponding to a first $\Delta BV$ % profile, a second zone corresponding to a second $\Delta BV$ % profile, and a third zone corresponding to a third $\Delta BV$ % profile.

In a further exemplary embodiment, the zone indicators are part of the GUI generated by the one or more controllers.

In a further exemplary embodiment, the zone indicators are part of an overlay attached to the display.

In a further exemplary embodiment, a controller of the sensor device is configured to determine the Hct values the $\Delta BV$ % values.

In a further exemplary embodiment, a controller of the display device is configured to determine the Hct values the $\Delta BV$ % values.

In a further exemplary embodiment, the system further includes: a remote device comprising another display, wherein the remote device is configured to receive the determined $\Delta BV$ % values and to display the $\Delta BV$ % plot on the display of the remote device; wherein zone indicators are also provided on the display of the remote device to distinguish between the first zone, the second zone, and the third zone.

In a further exemplary embodiment, the remote device is configured to monitor ΔBV % data from multiple dialysis systems corresponding to multiple patients.

In a further exemplary embodiment, the first ΔBV % profile corresponds to ΔBV % reduction being less than or equal to 3% per hour, wherein the second ΔBV % profile corresponds to ΔBV % reduction being greater than 3% per hour and less than or equal to 6.5% per hour and less than or equal to 15%, and wherein the third ΔBV % profile.

In a further exemplary embodiment, a controller of the display device is configured to generate the zone indicators at a predetermined time after the start of the dialysis treatment, and wherein the zone indicators are not provided before the predetermined time.

In a further exemplary embodiment, the zone indicators comprise a first boundary line indicating a boundary between the first zone and the second zone and a second boundary line indicating a boundary between the second zone and the third zone.

In a further exemplary embodiment, the first boundary line is generated by a controller of the display device based on a relationship y=−3x and the second boundary line is generated by the controller of the display device based on a relationship y=−6.5x up to a maximum of y=−15, wherein y corresponds to ΔBV % reduction and x corresponds to elapsed treatment time in hours.

In a further exemplary embodiment, determining a respective ΔBV % value is based on an initial hematocrit ($HCT_{T0}$) at an initial time of the dialysis treatment ($T_0$) and a current hematocrit measurement ($HCT_T$) at a current time (T).

In another exemplary embodiment, the present application provides a method for monitoring percentage change in blood volume (ΔBV %) during dialysis treatment. The method includes: obtaining, by a sensor device, hematocrit (Hct)-related measurements based on detecting light which has passed through extracorporeal blood of a patient undergoing the dialysis treatment; determining, by one or more controllers, Hct values based on the Hct-related measurements obtained by the sensor device; determining, by the one or more controllers, ΔBV % values based on the determined Hct values; generating, by the one or more controllers, a GUI having a ΔBV % plot based on the determined ΔBV % values; and displaying, by a display of a display device, the GUI having the ΔBV % plot. Zone indicators are provided on the display to distinguish between a first zone corresponding to a first ΔBV % profile, a second zone corresponding to a second ΔBV % profile, and a third zone corresponding to a third ΔBV % profile.

In a further exemplary embodiment, the zone indicators are part of the GUI generated by the one or more controllers.

In a further exemplary embodiment, the zone indicators are part of an overlay attached to the display.

In a further exemplary embodiment, the zone indicators are generated on the display at a predetermined time after the start of the dialysis treatment, and wherein the zone indicators are not provided before the predetermined time.

In yet another exemplary embodiment, the present application provides one or more non-transitory readable mediums having processor-executable instructions stored thereon for monitoring percentage change in blood volume (ΔBV %) during dialysis treatment. The processor-executable instructions, when executed, facilitate: obtaining, by a sensor device, hematocrit (Hct)-related measurements based on detecting light which has passed through extracorporeal blood of a patient undergoing the dialysis treatment; determining, by one or more controllers, Hct values based on the Hct-related measurements obtained by the sensor device; determining, by the one or more controllers, ΔBV % values based on the determined Hct values; generating, by the one or more controllers, a GUI having a ΔBV % plot based on the determined ΔBV % values, wherein the GUI further includes zone indicators to distinguish between a first zone corresponding to a first ΔBV % profile, a second zone corresponding to a second ΔBV % profile, and a third zone corresponding to a third ΔBV % profile; and displaying, by a display of a display device, the GUI having the ΔBV % plot.

In a further exemplary embodiment, generating the GUI comprises generating the zone indicators at a predetermined time after the start of the dialysis treatment.

In a further exemplary embodiment, the zone indicators comprise a first boundary line indicating a boundary between the first zone and the second zone and a second boundary line indicating a boundary between the second zone and the third zone.

In a further exemplary embodiment, the first boundary line is generated by a controller of the display device based on a relationship y=−3x and the second boundary line is generated by the controller of the display device based on a relationship y=−6.5x up to a maximum of y=−15, wherein y corresponds to ΔBV % reduction and x corresponds to elapsed treatment time in hours.

DETAILED DESCRIPTION

Figure 1:
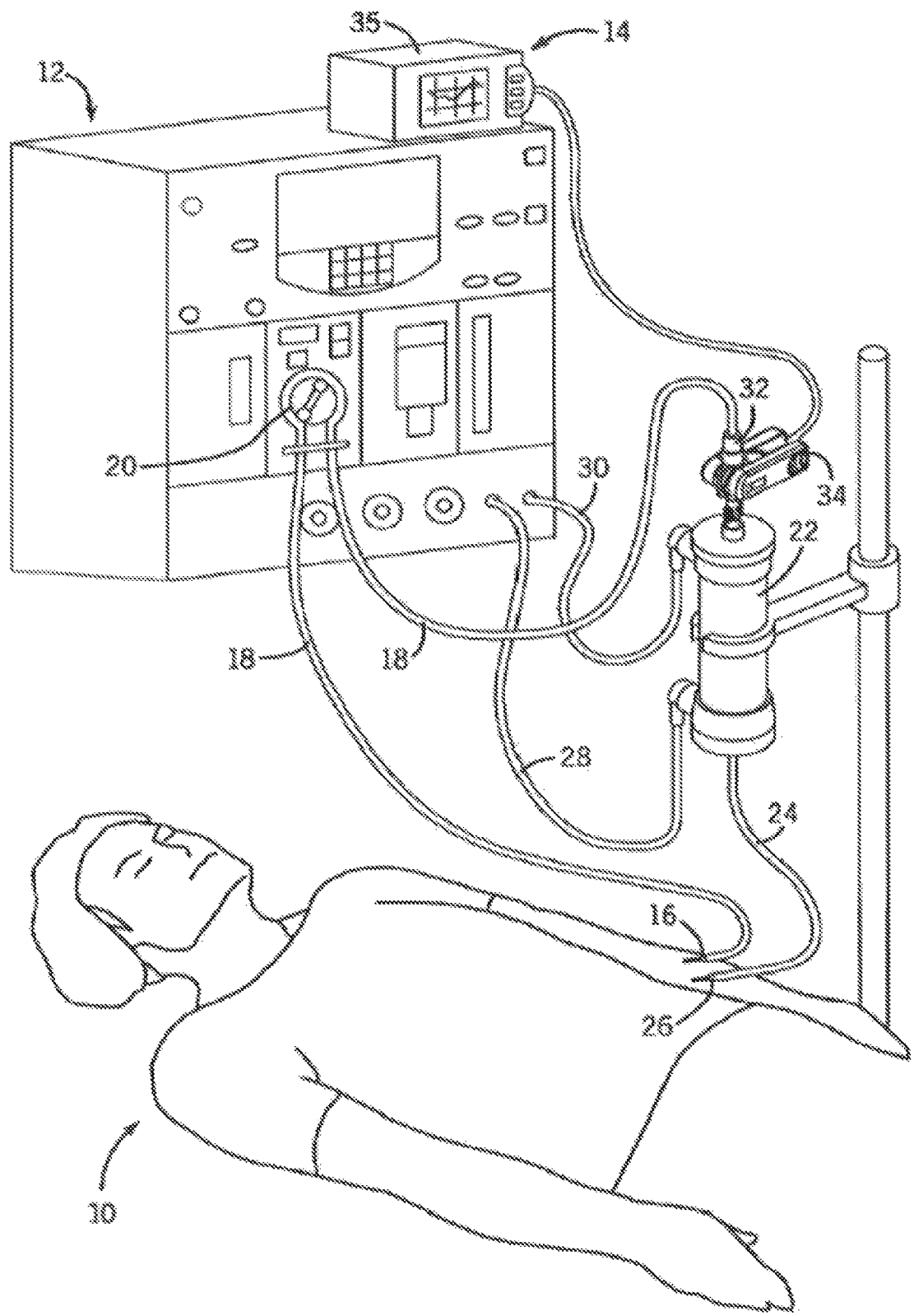
FIG. 1 is a schematic diagram of an exemplary hemodialysis system having an optical blood monitoring system.

It is advantageous to monitor the percentage change in blood volume (ΔBV %) during the course of a dialysis treatment to ensure that the treatment is safe and effective. There is a tradeoff between ultrafiltration rate (rate at which fluid is removed) versus risk of intradialytic complications (such as cramping, nausea, vomiting, lightheadedness, and hypotension).

If ΔBV % has a positive slope, is flat, or has a slightly negative slope, the patient's plasma refill rate is occurring at a greater rate, the same rate, or a slightly slower rate relative to the ultrafiltration rate of the dialysis treatment, which suggests that the ultrafiltration rate may be increased without immediate risk of symptoms. This corresponds to a profile where ΔBV % reduction is at or less than 3% per hour, and may be referred to as "Profile A."

If ΔBV % has a steep negative slope, the patient is experiencing a rapid decrease in blood volume (corresponding to a rapid increase in hemoconcentration of red blood cells), and the ultrafiltration rate is much higher than the plasma refill rate. This suggests that the patient is at higher risk of symptoms and an intervention may be necessary. This profile, where ΔBV % reduction is in excess of 6.5% per hour or 15%, may be referred to as "Profile C."

If ΔBV % profile has a gradual negative slope (i.e., more negative than Profile A but less negative than Profile C), the dialysis treatment is considered a good compromise for most patients between ultrafiltration rate and prevention of symptoms. This profile, where ΔBV % reduction is greater than 3% per hour and less than or equal to 6.5% per hour and less than or equal to 15%, may be referred to as "Profile B".

The ideal slope for each patient will vary based on patient-specific considerations, but in general, Profile C is too fast (thereby subjecting the patient to risk of intradialytic complications), and Profile A state is too slow (thereby increasing risk for fluid overload), so staying within Profile B during the dialysis treatment is optimal for most patients. There are some patients, however, which should stay within the Profile A state during a dialysis treatment due to certain issues such as cardiac instability.

Exemplary embodiments of the present application provide for a quick and effective way for medical professionals (such as nurses which are responsible for simultaneously managing the dialysis treatments of a large number of patients at a dialysis clinic) to determine, in real-time, whether ΔBV % for a patient at a current point in time corresponds to a Profile A state, a Profile B state, or a Profile C state, by plotting the ΔBV % for the patient in real-time together with zone indicators which facilitate visually distinguishing between Profile A, B, and C zones on the plot. For example, by including first and second boundary lines, starting on the plot 15 minutes into the dialysis treatment, which indicate the respective boundaries between Profile A-Profile B zones and Profile B-Profile C zones, the medical professionals are able to determine, at a glance, whether the ΔBV % for the patient at that point in time is within a desirable profile zone (e.g., the Profile B zone). This allows a medical professional to assess the status of the patient very quickly and in a reliable manner which is not prone to user error.

FIG. 1 is a schematic diagram of an exemplary hemodialysis system having an optical blood monitoring system. FIG. 1 depicts a patient 10 undergoing hemodialysis treatment using a hemodialysis machine 12. The hemodialysis system further includes an optical blood monitoring system 14.

An input needle or catheter 16 is inserted into an access site of the patient 10, such as in the arm, and is connected to extracorporeal tubing 18 that leads to a peristaltic pump 20 and to a dialyzer 22 (or blood filter). The dialyzer 22 removes toxins and excess fluid from the patient's blood. The dialyzed blood is returned from the dialyzer 22 through extracorporeal tubing 24 and return needle or catheter 26. Often, the extracorporeal blood flow may additionally receive a heparin drip to prevent clotting. The excess fluids and toxins are removed by clean dialysate liquid which is supplied to the dialyzer 22 via tube 28, and waste liquid is removed for disposal via tube 30. A typical hemodialysis treatment session takes about 3 to 5 hours in the United States.

The optical blood monitoring system 14 includes a display device 35 and a sensor device 34. The sensor device 34 may, for example, be a sensor clip assembly that is clipped to a blood chamber 32, wherein the blood chamber 32 is disposed in the extracorporeal blood circuit. A controller of the optical blood monitoring system 14 may be implemented in the display device 35 or in the sensor clip assembly 34, or both the display device 35 and the sensor clip assembly 34 may include a respective controller for carrying out respective operations associated with the optical blood monitoring system.

The blood chamber 32 may disposed in line with the extracorporeal tubing 18 upstream of the dialyzer 22. Blood from the peristaltic pump 20 flows through the tubing 18 into the blood chamber 32. The sensor device 34 includes emitters that emit light at certain wavelengths and detectors for receiving the emitted light after it has passed through the blood chamber 32. For example, the emitters may include LED emitters which emit light at approximately 810 nm, which is isobestic for red blood cells, at approximately 1300 nm, which is isobestic for water, and at approximately 660 nm, which is sensitive for oxygenated hemoglobin, and the detectors may include a silicon photodetector for detecting light at the approximately 660 and 810 nm wavelengths, and an indium gallium arsenide photodetector for detecting light at the approximately 1300 nm wavelength. The blood chamber 32 includes lenses or viewing windows that allows the light to pass through the blood chamber 32 and the blood flowing therein.

A controller of the optical blood monitoring system 14 uses the light intensities measured by the detectors to determine Hct values for blood flowing through the blood chamber 32. The controller calculates hematocrit, oxygen saturation, and change in blood volume associated with blood passing through the blood chamber 32 to which the sensor device 34 is attached using a ratiometric model. The intensity of the received light at each of the various wavelengths is reduced by attenuation and scattering from the fixed intensity of the visible and infrared light emitted from each of the LED emitters. Beer's Law, for each wavelength of light, describes attenuation and scattering as follows:

$$i_n = I_{0-n} * e^{-\epsilon_p X_p d_{pt}} * e^{-\epsilon_b X_b d_b} * e^{-\epsilon_p X_p d_{pr}} \quad (1)$$

where $i_n$=received light intensity at wavelength n after attenuation and scattering; $I_{0-n}$=transmitted light intensity at wavelength n incident to the measured medium; e=the natural exponential term; ε=the extinction coefficient for the measured medium (p—blood chamber polycarbonate, b—blood); X=the molar concentration of the measured medium (p—blood chamber polycarbonate, b—blood); and d=the distance through the measured medium (pt—transmitting blood chamber polycarbonate, b—blood, pr—receiving blood chamber polycarbonate).

Since the properties of the polycarbonate blood chamber do not change, the first and third exponential terms in the above Eq. (1) are constants for each wavelength. Mathematically, these constant terms are multiplicative with the initial constant term $I_{0-n}$ which represents the fixed intensity of the radiation transmitted from a respective LED emitter. For simplification purposes, Eq. (1) can be rewritten in the following form using bulk extinction coefficients and a modified initial constant $I'_{0-n}$ as follows:

$$i_n = I'_{0-n} * e^{-\alpha_b d_b} \quad \text{Eq. (2)}$$

where $i_n$=received light intensity at wavelength "n" after attenuation and scattering as though the detector were at the receive blood boundary; α=the bulk extinction coefficient ($\alpha_b = \epsilon_b X_b$) and $I'_{0-n}$=the equivalent transmitted light intensity at wavelength n as if applied to the transmit blood boundary accounting for losses through the blood chamber. Note that the term $I'_{0-n}$ is the light intensity incident on the blood with the blood chamber losses included.

Using the approach defined in Eq. (2) above, the 810 nm wavelength which is isobestic for red blood cells and the 1300 nm wavelength which is isobestic for water can be used to determine the patient's hematocrit. The ratio of the normalized amplitudes of the measured intensity at these two wavelengths produces the ratio of the composite extinction values a for the red blood cells and the water constituents in the blood chamber, respectively. A mathematical function then defines the measured HCT value:

$$HCT = f\left[\frac{\ln\left(\frac{i_{810}}{I_{0-810}}\right)}{\ln\left(\frac{i_{1300}}{I_{0-1300}}\right)}\right] \quad \text{Eq. (3)}$$

where $i_{810}$ is the light intensity of the photo receiver at 810 nm, $i_{1300}$ is the infrared intensity of the photodetector at 1300 nm and $I_{0-810}$ and $I_{0-1300}$ are constants representing the intensity incident on the blood accounting for losses through the blood chamber. The above equation holds true assuming that the flow of blood through the blood chamber 32 is in steady state, i.e. steady pressure and steady flow rate.

The preferred function f[ ] is a second order polynomial having the following form:

$$HCT = f\left[\frac{\ln\left(\frac{i_{810}}{I_{0-810}}\right)}{\ln\left(\frac{i_{1300}}{I_{0-1300}}\right)}\right] = A\left[\frac{\ln\left(\frac{i_{810}}{I_{0-810}}\right)}{\ln\left(\frac{i_{1300}}{I_{0-1300}}\right)}\right]^2 + B\left[\frac{\ln\left(\frac{i_{810}}{I_{0-810}}\right)}{\ln\left(\frac{i_{1300}}{I_{0-1300}}\right)}\right] + C. \quad \text{Eq. (4)}$$

A second order polynomial is normally adequate as long as the infrared radiation incident at the first and second wavelengths is substantially isobestic.

The oxygen saturation level, or the oxygenated hemoglobin level, is determined with a ratiometric model having the following form:

$$SAT = g\left[\frac{\ln\left(\frac{i_{660}}{I_{0-660}}\right)}{\ln\left(\frac{i_{810}}{I_{0-810}}\right)}\right] \quad \text{Eq. (5)}$$

where $i_{660}$ is the light intensity of the photo receiver at 660 nm, $i_{810}$ is the intensity of the photodetector at 810 nm and $I_{0-660}$ and $I_{0-810}$ are constants representing the intensity incident on the blood accounting for losses through the blood chamber. The function g[•] is a mathematical function determined based on experimental data to yield the oxygen saturation level, again preferably a second order polynomial. It may be useful to use a pair of second order polynomials depending on the hematocrit value or a separate 810 nm calibration for oxygen and hematocrit.

ΔBV % for the patient is determined based on an initial hematocrit measurement ($HCT_{T0}$) at an initial time of the treatment ($T_0$) relative to a current hematocrit measurement ($HCT_T$) at a current time (T), for example, according to the following formula:

ΔBV %=[($HCT_{T0}$/$HCT_T$)−1]*100.

The display device 35 may be used to display determined values of hematocrit, oxygen saturation, and percentage change in blood volume for a patient during hemodialysis treatment, and a displayed GUI provided by the display device 35 may include a plot of ΔBV % over time. Further, the display device 35 and/or the sensor device 34 may include communications hardware and/or interfaces for communicating the determined values of hematocrit, oxygen saturation, and change in blood volume to one or more other devices.

The hemodialysis system depicted in FIG. 1 may be one of a plurality of hemodialysis systems in a dialysis clinic. Patients may come into the dialysis clinic for treatments at regular intervals, for example, on a Monday-Wednesday-Friday schedule or a Tuesday-Thursday-Saturday schedule.

It will be appreciated that the hemodialysis system depicted in FIG. 1 is merely exemplary, and that the principles discussed herein may be applicable to other types of hemodialysis systems, dialysis systems or medical devices and systems.

Figure 2A:
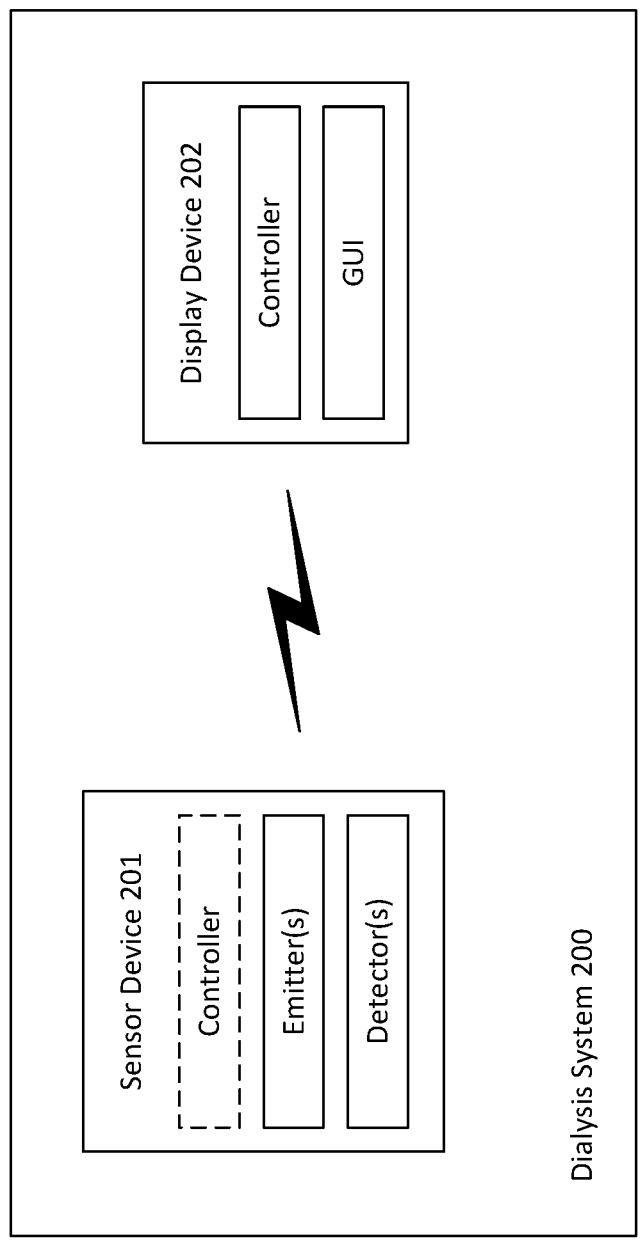
FIGS. 2A-2B are block diagrams illustrating exemplary system configurations for monitoring and/or controlling one or more dialysis machines during dialysis treatment.
Figure 2B:
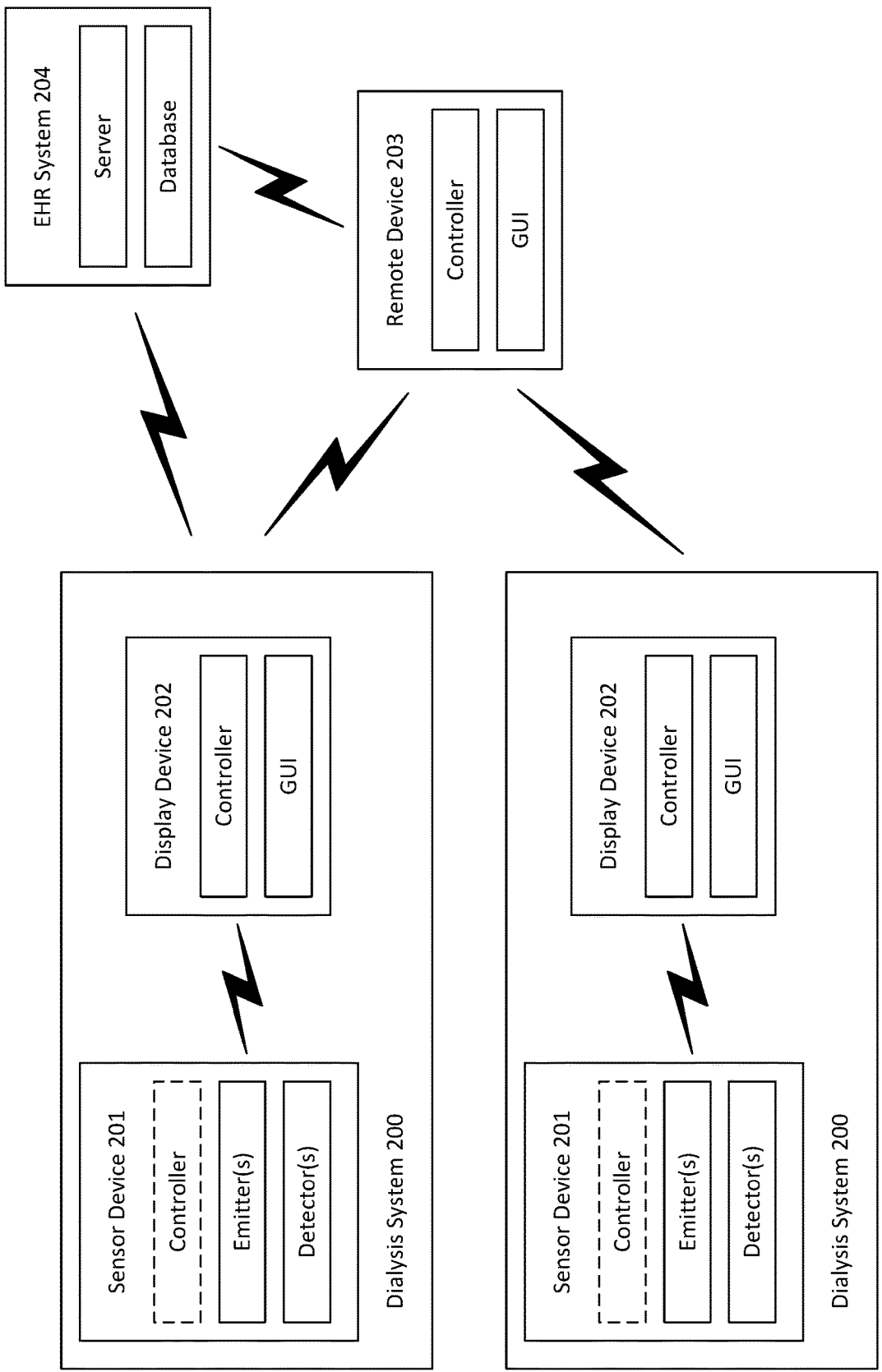

FIGS. 2A-2B are block diagrams illustrating exemplary system configurations for monitoring and/or controlling one or more dialysis machines during dialysis treatment.

FIG. 2A is a block diagram depicting a dialysis system 200 which includes, among other components and devices, a sensor device 201 configured for measuring hematocrit (e.g., sensor device 34 depicted in FIG. 1) and a display device 202 configured for providing a graphical user interface (GUI) (e.g., display device 35 depicted in FIG. 1). The sensor device 201 includes emitter(s) and detector(s) to facilitate hematocrit measurement, and the sensor device 201 may further include a controller configured to calculate Hct and/or ΔBV % based on signals measured by the detector(s), and the sensor device 201 provides the calculated Hct and/or ΔBV % information to the display device 202 via a wired or wireless connection. Alternatively, the sensor device 201 does not include a controller, and the operation of the emitter(s) and detector(s), as well as calculation of Hct and ΔBV % values, are performed by a controller of the display device 202, with the display device 202 sending control signals to and receiving raw data from the sensor device 201 via a wired or wireless connection. The controller of the display device 202 is further configured to generate the GUI which is output on a display of the display device 202.

FIG. 2B is a block diagram depicting multiple dialysis systems 200 in communication with a remote device 203 configured for remotely monitoring and/or controlling one or more dialysis systems. The remote device 203 may be, for example, a centralized computing device at a dialysis clinic from which a medical professional is able to remotely monitor and/or control multiple dialysis systems 200 of the dialysis clinic, wherein each dialysis system 200 includes, among other components and devices, a sensor device 201 and a display device 202 as discussed above in connection with FIG. 2A. The remote device 203, may communicate with display devices 202 and/or with sensor devices 201 to obtain raw data, Hct and/or ΔBV % data via a wired or wireless connection, and the remote device 203 may include a controller configured to perform Hct and/or ΔBV % calculations and/or to generate a GUI for output on a display of the remote device 203. The GUI of the remote device 203 may provide for simultaneous display of ΔBV % plots for multiple dialysis systems 200, and/or for toggling between displaying respective ΔBV % plots for respective dialysis systems 200.

The display devices 202 and/or the remote device 203 may further communicate with an electronic health records (EHR) system 204 via a communication network (e.g., the Internet) to provide patient information for storage in the EHR system 204 and/or to obtain patient information from the EHR system 204. The EHR system 204 may include, for example, a server and a database.

Figure 3:
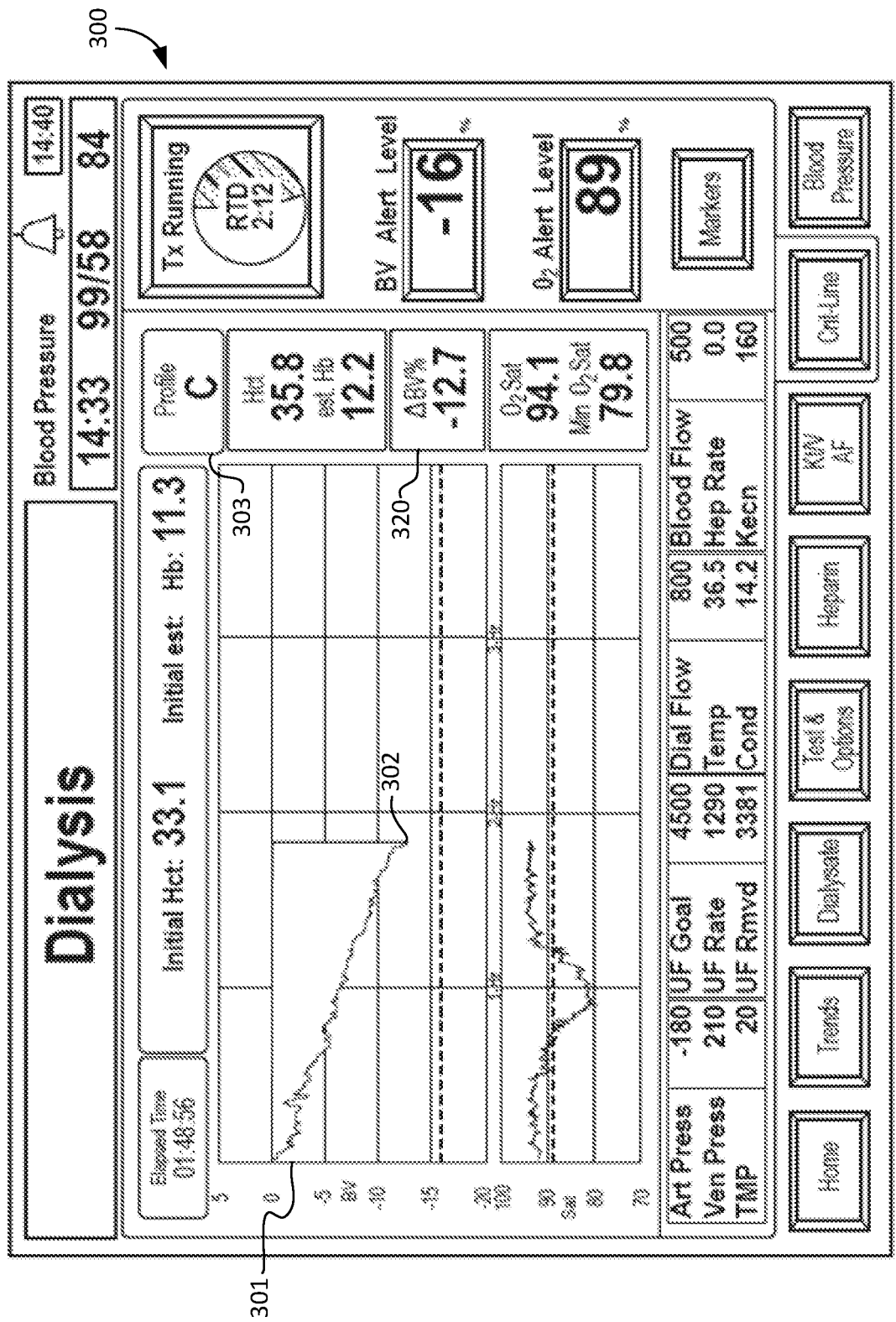
FIG. 3 is an illustrative example of a conventional graphical user interface (GUI) for monitoring and/or controlling a dialysis machine during dialysis treatment.

FIG. 3 is an illustrative example of a conventional GUI 300 for monitoring and/or controlling a dialysis machine during dialysis treatment. The GUI 300 includes a ΔBV % plot 301 indicating ΔBV % data 302 over the course of the dialysis treatment up to a current point in time. A current ΔBV % value corresponding to the current point in time is also indicated in box 320. In this example, the treatment has been running for one hour, 48 minutes, and 56 seconds ("Elapsed Time 01:48:56"), and the ΔBV % value at the current point in time is −12.7%.

The GUI 300 further includes a profile indication box 303 which outputs a determined profile out of Profile A, Profile B or Profile C based on the amount of percentage blood volume loss over the past 15 minutes. At the current point in time, the profile indication box 303 indicates that the past 15 minutes of treatment for the patient correspond to "Profile C."

GUI 300 also provides other monitoring information relating to the ongoing dialysis treatment, such as an oxygen saturation plot, hematocrit information, and estimated hemoglobin information. Further, GUI 300 also provides other monitoring and control options, such as an option to set a blood volume percentage loss alert level, an option to set an oxygen saturation alert level, and options to navigate to other GUIs relating to the dialysis treatment.

Figure 4:
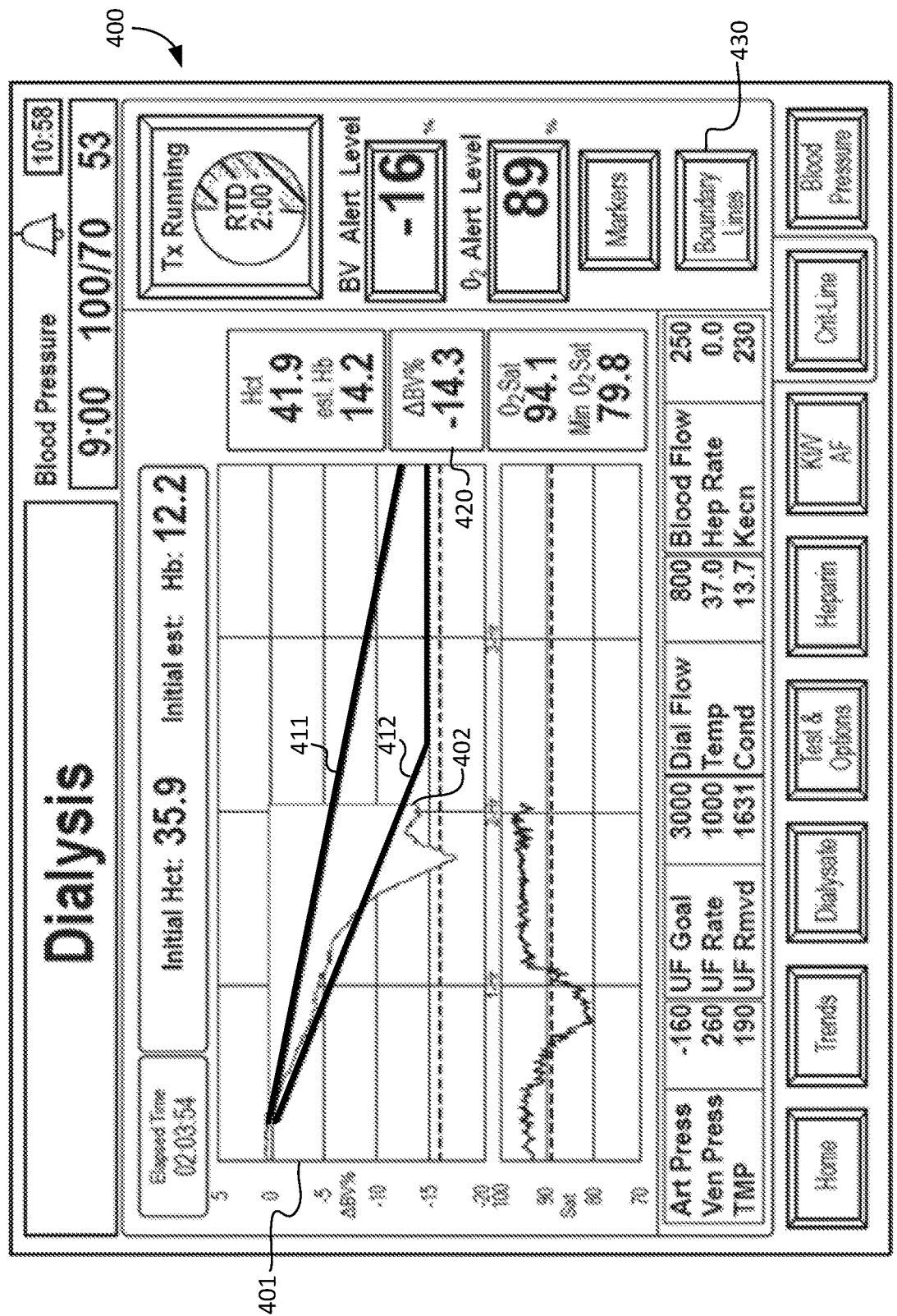
FIG. 4 is an illustrative example of a GUI for monitoring and/or controlling a dialysis machine during dialysis treatment in accordance with an exemplary embodiment of the present application.

FIG. 4 is an illustrative example of a GUI 400 for monitoring and/or controlling a dialysis machine during dialysis treatment in accordance with an exemplary embodiment of the present application. The GUI 400 includes a ΔBV % plot 401 indicating ΔBV % data 402 over the course of the dialysis treatment up to a current point in time. A current ΔBV % value corresponding to the current point in time is also indicated in box 420. In this example, the treatment has been running for two hours, three minutes, and 54 seconds ("Elapsed Time 02:03:54"), and the ΔBV % value at the current point in time is −14.3%.

The GUI 400 further includes a first boundary line 411 and a second boundary line 412 overlaid on the ΔBV % plot 401 which act as zone indicators for distinguishing between a Profile A zone, a Profile B zone, and a Profile C zone on the plot. The Profile A zone on the ΔBV % plot 401 corresponds to the area of the plot above the first boundary line 411, the Profile B zone on the ΔBV % plot 401 corresponds to the area of the plot between the first boundary line 411 and the second boundary line 412, and the Profile C zone on the ΔBV % plot 401 corresponds to the area of the plot below the second boundary line 412.

Display of the first and second boundary lines 411, 412 on the ΔBV % plot 401 may be toggled on or off based on user interaction with a "Boundary Lines" button 430 on the GUI 400. For example, the first and second boundary lines 411, 412 may start off as not being displayed, and in response to a user pressing down on the "Boundary Lines" button 430 on a touchscreen corresponding to the GUI 400, the first and second boundary lines 411, 412 are then displayed, and the "Boundary Lines" button 430 is shown as being in a depressed state until it is pressed again (and in response to be pressed again while in the depressed state, the first and second boundary lines 411, 412 are then no longer displayed, and the "Boundary Lines" button 430 is switched to an un-pressed state). Alternatively, the default configuration of the ΔBV % plot 401 may include the first and second boundary lines 411, 412 being displayed, and the user may press down on the "Boundary Lines" button 430 on the touchscreen corresponding to the GUI 400 to cause the display of the first and second boundary lines 411, 412 to be turned off.

GUI 400 also provides other monitoring information relating to the ongoing dialysis treatment, such as an oxygen saturation plot, hematocrit information, and estimated hemoglobin information. Further, GUI 400 also provides other monitoring and control options, such as an option to set a blood volume percentage loss alert level, an option to set an oxygen saturation alert level, and options to navigate to other GUIs relating to the dialysis treatment.

In an exemplary embodiment, the first boundary line 411 and the second boundary line 412 are provided in a different color relative to the color of the ΔBV % data 402 in the ΔBV % plot 401. For example, the ΔBV % data 402 may be shaded blue, while the first boundary line 411 and the second boundary line 412 are provided in orange so as to provide visual contrast.

By incorporating the first boundary line 411 and the second boundary line 412, the GUI 400 of FIG. 4 provides for various advantages over the GUI 300 of FIG. 3. For example, by looking at the GUI 400 of FIG. 4, a medical professional can quickly and clearly ascertain whether the ΔBV % data 402 for a patient corresponds to Profile A, B or C, as well as whether there were any anomalies during the course of the treatment (e.g., in the example of FIG. 4, there was a steep dip in ΔBV % at around 1:30-1:45 into the treatment, resulting in the triggering of a ΔBV %-related alert, after which the ultrafiltration rate was slowed down to allow plasma refill to occur at a rate greater than the ultrafiltration rate, but before the patient could get back into the desirable Profile B zone, the ΔBV % started dipping down again). The medical professional would not have been able to readily discern the crossings between the Profile B and Profile C zones using the GUI 300 of FIG. 3, and the medical professional further may have been confused by the profile indicator box 320 (e.g., there may be a situation where the profile indicator box 320 indicates that the last 15 minutes of dialysis treatment correspond to "Profile C," but the ΔBV % data 402 may actually still be safely within the Profile B zone or the Profile A zone, such that the medical professional erroneously determines that intervention is needed when intervention might not actually be appropriate).

Given that there are often a small number of medical professionals responsible for a large number of patients simultaneously undergoing dialysis treatments, the amount of time that each medical professional is able to spending checking on each respective patient may be very limited. Thus, being able to quickly and clearly ascertain whether the ΔBV % data for a patient falls within a Profile A zone, a Profile B zone, or a Profile C zone (as well as being able to quickly ascertain the trajectory of ΔBV % over time within or across the zone(s)) provides a significant improvement with respect to the provision of safe and effective dialysis treatment.

Figure 5:
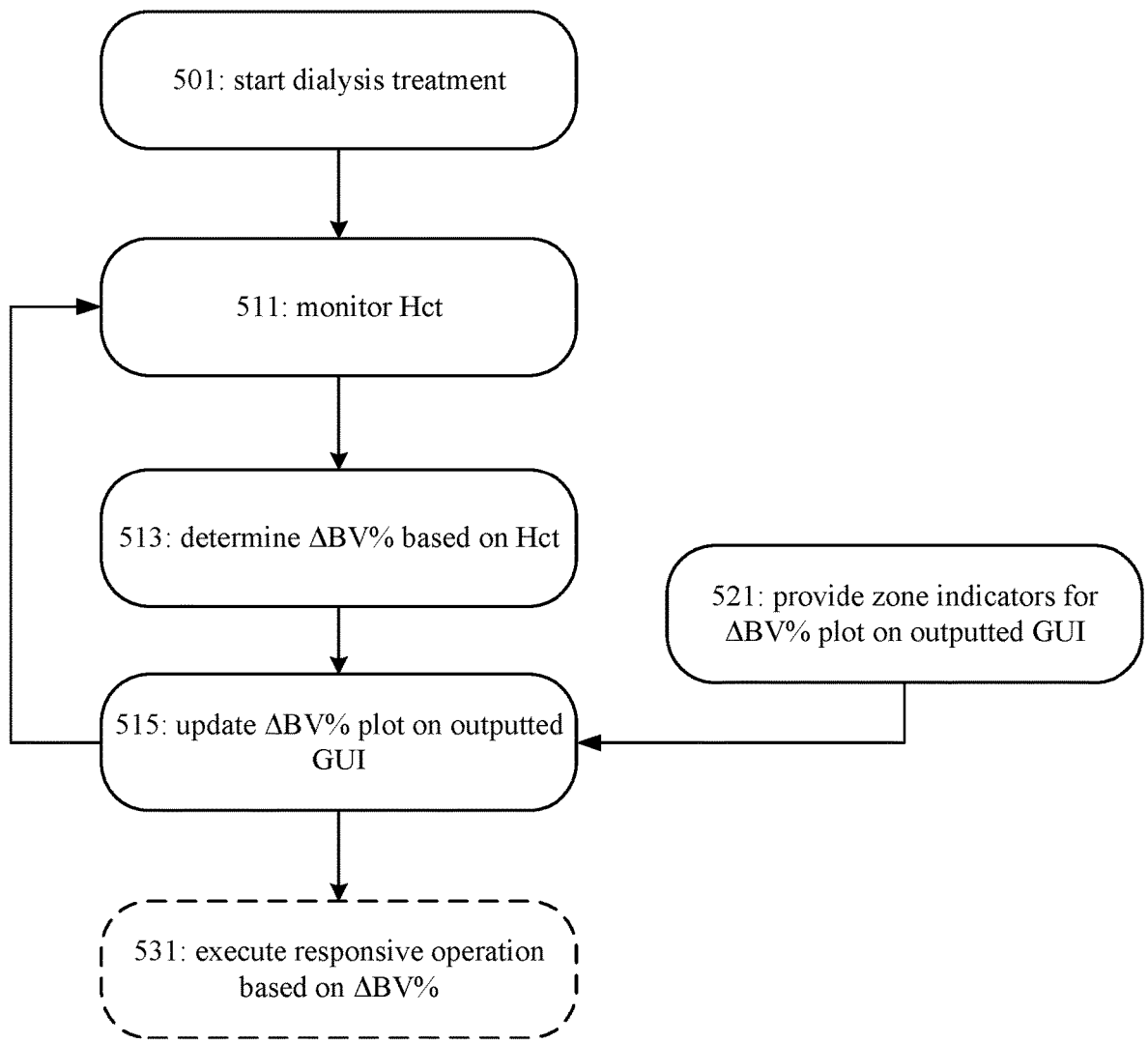
FIG. 5 is a flowchart illustrating a process for plotting ΔBV % information during the course of a dialysis treatment for a respective patient in accordance with an exemplary embodiment of the present application.

FIG. 5 is a flowchart illustrating a process for plotting ΔBV % information during the course of a dialysis treatment for a respective patient in accordance with an exemplary embodiment of the present application. At stage 501, the dialysis treatment is started for the patient, for example, by using a dialysis machine such as the dialysis machine 12 depicted in FIG. 1. At stage 511, an optical blood monitoring system, such as optical blood monitoring system 14 as depicted in FIG. 1, is used to monitor Hct, for example, by obtaining Hct-related measurements using a sensor device such as sensor device 34 as depicted in FIG. 1. At stage 513, a controller, such as a controller of sensor device 34 or a controller of display device 35 as depicted in FIG. 1, determines ΔBV % values using measured Hct values, for example in the manner discussed above in connection with FIG. 1. At stage 515, a controller, such as the controller of display device 35, updates a ΔBV % plot on an outputted GUI, such as a GUI generated by the controller of the display device 35.

At stage 521, zone indicators for the ΔBV % plot, such as the boundary lines depicted in FIG. 4, are provided on the outputted GUI. In an exemplary implementation, the zone indicators are generated by a controller, such as the controller of display device 35, and displayed as part of the ΔBV % plot of the GUI. In an example, the zone indicators (e.g., boundary lines) are not displayed until a predetermined amount of time into the treatment (e.g., 15 minutes into the treatment), to avoid premature intervention.

Optionally, at stage 531, a responsive operation may be executed by a controller of the dialysis system based on determined ΔBV % information. For example, an alert or notification may be triggered based on the determined ΔBV % value at stage 513 exceeding a predetermined threshold, and/or based on the controller determining that the ΔBV % data has crossed from one zone into another zone (e.g., from the Profile B zone into the Profile C zone). In addition to or alternatively to the alert or notification, other responsive operations may also be performed, such as adjustment of the dialysis treatment in response to the determined ΔBV % value at stage 513 exceeding a predetermined threshold, and/or in response to the controller determining that the ΔBV % data has crossed from one zone into another zone, or in response to determining that the patient has been in the Profile C zone for a predetermined amount of time. For example, the ultrafiltration rate may be decreased or the dialysis treatment may be paused or stopped in response to determining that the ΔBV % data has crossed from Profile B into Profile C, or in response to determining that the patient has been in the Profile C zone for a predetermined amount of time.

In an exemplary implementation, the zone indicators are first and second boundary lines as depicted and discussed above with respect to FIG. 4. The ΔBV % plot includes an x-axis corresponding to time (e.g., in hours), and a y-access corresponding to ΔBV %. The first zone boundary line 411 may be generated on the ΔBV % plot for the time period corresponding to 15 minutes into the treatment to 4 hours into the treatment as shown in FIG. 4 based on the formula y=−3x such that the first boundary line 411 crosses the following points in Table 1:

TABLE 1

| Elapsed Time (Hrs) | ΔBV% |
|---|---|
| 0.25 | −0.75 |
| 0.5 | −1.5 |
| 0.75 | −2.25 |
| 1 | −3 |
| 1.25 | −3.75 |
| 1.5 | −4.5 |
| 1.75 | −5.25 |
| 2 | −6 |
| 2.25 | −6.75 |
| 2.5 | −7.5 |
| 2.75 | −8.25 |
| 3 | −9 |
| 3.25 | −9.75 |
| 3.5 | −10.5 |
| 3.75 | −11.25 |
| 4 | −12 |

The second boundary line 412 may be generated on the ΔBV % plot for the time period corresponding to 15 minutes into the treatment to 4 hours into the treatment as shown in FIG. 4 based on the formula: y=−6.5x up to a maximum of y=−15 such that the first zone boundary line 412 crosses the following points in Table 2:

TABLE 2

| Elapsed Time (Hrs) | ΔBV% |
|---|---|
| 0.25 | −1.625 |
| 0.5 | −3.25 |
| 0.75 | −4.875 |
| 1 | −6.5 |
| 1.25 | −8.125 |
| 1.5 | −9.75 |
| 1.75 | −11.375 |
| 2 | −13 |
| 2.25 | −14.625 |
| 2.5 | −15 |
| 2.75 | −15 |
| 3 | −15 |
| 3.25 | −15 |
| 3.5 | −15 |
| 3.75 | −15 |
| 4 | −15 |

Figure 6:
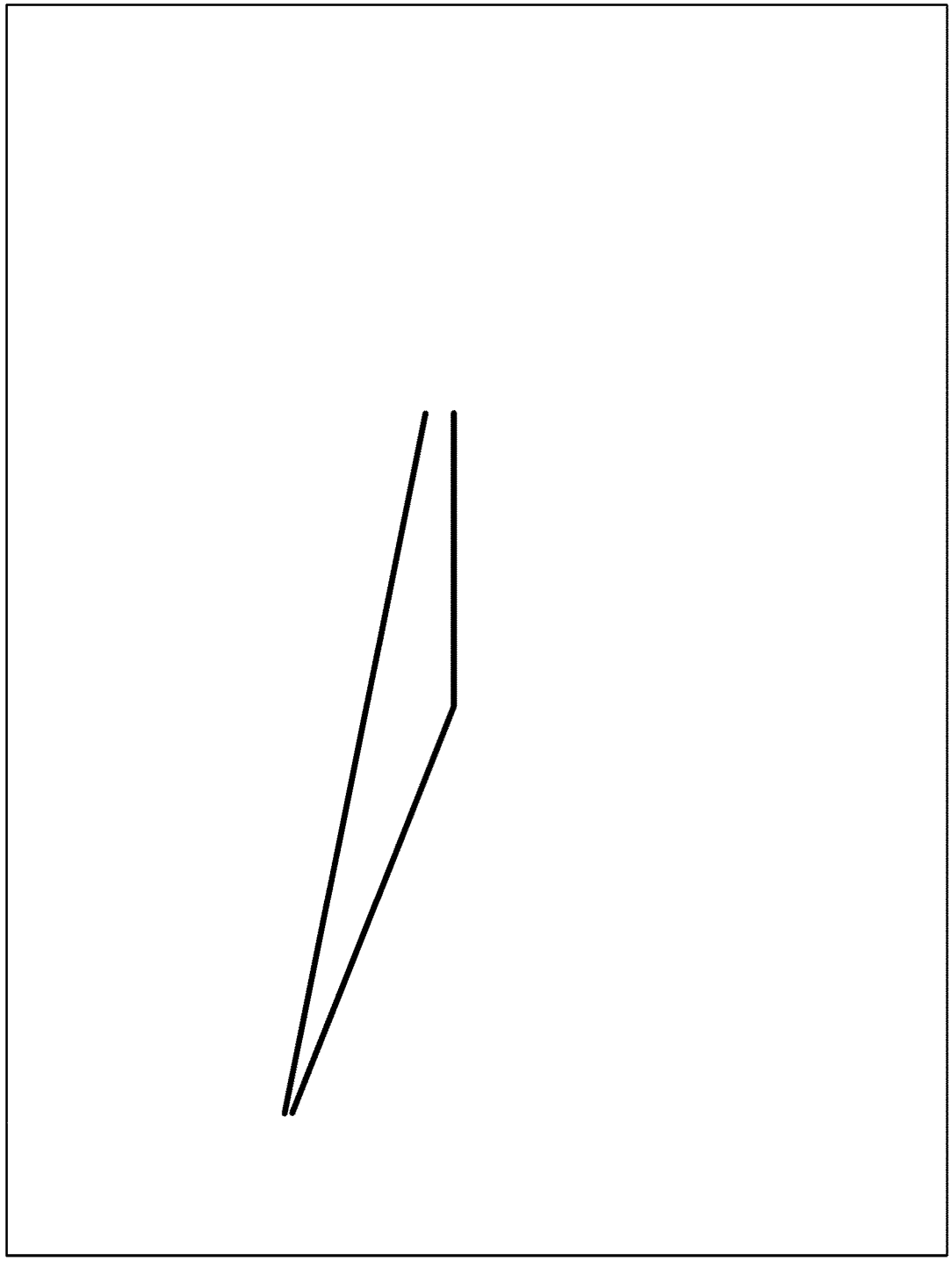
FIG. 6 depicts an example of a transparent film having boundary lines drawn or printed thereon.

In an alternative embodiment of the present application, the provision of the zone indicators (e.g., boundary lines) at stage 521 of FIG. 5 may be based on providing a physical overlay for a screen corresponding to the GUI, for example, by attaching a transparent film having the boundary lines drawn or printed thereon onto the screen. An example of a transparent film having the boundary lines drawn or printed thereon is shown in FIG. 6. The transparent film may, for example, have an adhesive side for attaching the film to a screen.

Although the examples discussed above utilize boundary lines as zone indicators, it will be appreciated that other types of zone indicators may be used as well. For example, differently shaded, patterned and/or colored regions corresponding to each zone may be utilized in addition to or instead of boundary lines. Reference labels (e.g., "A", "B", and "C") may also be included in each respective zone.

Exemplary embodiments of the present application provide for utilizing zone indicators, such as boundary lines, in a ΔBV % plot output as part of a GUI, such that a medical professional is able to quickly and clearly ascertain whether ΔBV % data for a patient corresponds to a Profile A zone, a Profile B zone, or a Profile C zone, as well as being able to quickly evaluate the trajectory of ΔBV % over time within or across the zone(s). This provides a significant improvement with respect to the provision of safe and effective dialysis treatment, especially in situations where a small number of medical professionals are responsible for a large number of patients simultaneously undergoing dialysis treatments such that the amount of time that can be spent checking on each respective patient may be very limited.

It will be appreciated that the various machine-implemented operations described herein may occur via the execution, by one or more respective processors, of processor-executable instructions stored on a tangible, non-transitory computer-readable medium, such as a random access memory (RAM), read-only memory (ROM), programmable read-only memory (PROM), and/or another electronic memory mechanism. Thus, for example, operations performed by any device described herein may be carried out according to instructions stored on and/or applications installed on the device, and via software and/or hardware of the device.

All references, including publications, patent applications, and patents, cited herein are hereby incorporated by reference to the same extent as if each reference were individually and specifically indicated to be incorporated by reference and were set forth in its entirety herein.

While the invention has been illustrated and described in detail in the drawings and foregoing description, such illustration and description are to be considered illustrative or exemplary and not restrictive. It will be understood that changes and modifications may be made by those of ordinary skill within the scope of the following claims. In particular, the present application covers further embodiments with any combination of features from different embodiments described above and below.

The terms used in the claims should be construed to have the broadest reasonable interpretation consistent with the foregoing description. For example, the use of the article "a" or "the" in introducing an element should not be interpreted as being exclusive of a plurality of elements. Likewise, the recitation of "or" should be interpreted as being inclusive, such that the recitation of "A or B" is not exclusive of "A and B," unless it is clear from the context or the foregoing description that only one of A and B is intended. Further, the recitation of "at least one of A, B and C" should be interpreted as one or more of a group of elements consisting of A, B and C, and should not be interpreted as requiring at least one of each of the listed elements A, B and C, regardless of whether A, B and C are related as categories or otherwise. Moreover, the recitation of "A, B and/or C" or "at least one of A, B or C" should be interpreted as including any singular entity from the listed elements, e.g., A, any subset from the listed elements, e.g., A and B, or the entire list of elements A, B and C.

Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

The invention claimed is:

1. A system for monitoring percentage change in blood volume (ΔBV %) during dialysis treatment, comprising:
    a sensor device configured to obtain hematocrit (Hct)-related measurements based on detecting light which has passed through extracorporeal blood of a patient undergoing the dialysis treatment;
    one or more controllers configured to:
        determine Hct values based on the Hct-related measurements obtained by the sensor device;
        determine ΔBV % values based on the determined Hct values; and
        generate a graphical user interface (GUI) having a ΔBV % plot based on the determined ΔBV % values, wherein generating the GUI having the ΔBV % plot includes generating zone indicators to distinguish between a first zone corresponding to a first ΔBV % profile, a second zone corresponding to a second ΔBV % profile, and a third zone corresponding to a third ΔBV % profile; and
    a display device having a display configured to display the GUI having the ΔBV % plot;
    wherein a controller of the display device is configured to generate the zone indicators at a predetermined time after the start of the dialysis treatment, and wherein the zone indicators are not provided before the predetermined time.

2. The system according to claim 1, wherein a controller of the sensor device is configured to determine the Hct values and the ΔBV % values.

3. The system according to claim 1, wherein the controller of the display device is configured to determine the Hct values and the ΔBV % values.

4. The system according to claim 1, further comprising:
    a remote device comprising another display, wherein the remote device is configured to receive the determined ΔBV % values and to display the ΔBV % plot on the display of the remote device with zone indicators to distinguish between the first zone, the second zone, and the third zone.

5. The system according to claim 4, wherein the remote device is configured to monitor ΔBV % data from multiple dialysis systems corresponding to multiple patients.

6. The system according to claim 1, wherein the first ΔBV % profile corresponds to ΔBV % reduction being less than or equal to 3% per hour, wherein the second ΔBV % profile corresponds to ΔBV % reduction being greater than 3% per hour and less than or equal to 6.5% per hour and less than or equal to 15%, and wherein the third ΔBV % profile corresponds to ΔBV % reduction greater than 6.5% per hour or greater than 15%.

7. The system according to claim 1, wherein the zone indicators comprise a first boundary line indicating a boundary between the first zone and the second zone and a second boundary line indicating a boundary between the second zone and the third zone.

8. The system according to claim 7, wherein the first boundary line is generated by the controller of the display device based on a relationship y=−3x and the second boundary line is generated by the controller of the display device based on a relationship y=−6.5x up to a maximum of y=−15, wherein y corresponds to ΔBV % reduction and x corresponds to elapsed treatment time in hours.

9. The system according to claim 1, wherein determining a respective ΔBV % value is based on an initial hematocrit ($HCT_{T0}$) at an initial time of the dialysis treatment ($T_0$) and a current hematocrit measurement ($HCT_T$) at a current time (T).

10. A method for monitoring percentage change in blood volume (ΔBV %) during dialysis treatment, comprising:
    obtaining, by a sensor device, hematocrit (Hct)-related measurements based on detecting light which has passed through extracorporeal blood of a patient undergoing the dialysis treatment;
    determining, by one or more controllers, Hct values based on the Hct-related measurements obtained by the sensor device;
    determining, by the one or more controllers, ΔBV % values based on the determined Hct values;
    generating, by the one or more controllers, a graphical user interface (GUI) having a ΔBV % plot based on the determined ΔBV % values; and
    displaying, by a display of a display device, the GUI having the ΔBV % plot;
    wherein zone indicators are provided on the display to distinguish between a first zone corresponding to a first ΔBV % profile, a second zone corresponding to a second ΔBV % profile, and a third zone corresponding to a third ΔBV % profile;

wherein the zone indicators are generated on the display at a predetermined time after the start of the dialysis treatment, and wherein the zone indicators are not provided before the predetermined time.

11. The method according to claim 10, wherein the zone indicators are part of the GUI generated by the one or more controllers.

12. The method according to claim 10, wherein the zone indicators are part of an overlay attached to the display.

13. One or more non-transitory computer-readable mediums having processor-executable instructions stored thereon for monitoring percentage change in blood volume (ΔBV %) during dialysis treatment, wherein the processor-executable instructions, when executed, facilitate:

obtaining, by a sensor device, hematocrit (Hct)-related measurements based on detecting light which has passed through extracorporeal blood of a patient undergoing the dialysis treatment;

determining, by one or more controllers, Hct values based on the Hct-related measurements obtained by the sensor device;

determining, by the one or more controllers, ΔBV % values based on the determined Hct values;

generating, by the one or more controllers, a graphical user interface (GUI) having a ΔBV % plot based on the determined ΔBV % values, wherein the GUI further includes zone indicators to distinguish between a first zone corresponding to a first ΔBV % profile, a second zone corresponding to a second ΔBV % profile, and a third zone corresponding to a third ΔBV % profile; and displaying, by a display of a display device, the GUI having the ΔBV % plot;

wherein generating the GUI comprises generating the zone indicators at a predetermined time after the start of the dialysis treatment.

14. The one or more non-transitory computer-readable mediums according to claim 13, wherein the zone indicators comprise a first boundary line indicating a boundary between the first zone and the second zone and a second boundary line indicating a boundary between the second zone and the third zone.

15. The one or more non-transitory computer-readable mediums according to claim 14, wherein the first boundary line is generated by a controller of the display device based on a relationship $y=-3x$ and the second boundary line is generated by the controller of the display device based on a relationship $y=-6.5x$ up to a maximum of $y=-15$, wherein y corresponds to ΔBV % reduction and x corresponds to elapsed treatment time in hours.

16. The system according to claim 1, wherein the second ΔBV % profile corresponds to a desirable amount of blood volume decrease during the dialysis treatment, wherein the first ΔBV % profile corresponds to a lesser amount of blood volume decrease than the second ΔBV % profile, and wherein the third ΔBV % profile corresponds to a greater amount of blood volume decrease than the second ΔBV % profile.

* * * * *